United States Patent
Goulu et al.

(10) Patent No.: US 10,390,532 B2
(45) Date of Patent: *Aug. 27, 2019

(54) INSECTICIDE COMPOSITION INCLUDING THIAMETHOXAM AND A SYNERGISTIC AGENT

(71) Applicant: UNIVERSITE D'ANGERS, Angers (FR)

(72) Inventors: Mathilde Goulu, Fontaine-Milon (FR); Véronique Apaire-Marchais, Angers (FR); Olivier List, Galcon (FR); Valérie Raymond, Bouchemaine (FR); Bruno Lapied, Angers (FR)

(73) Assignee: UNIVERSITE D'ANGERS, Angers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/780,881

(22) PCT Filed: Dec. 2, 2016

(86) PCT No.: PCT/EP2016/079608
§ 371 (c)(1),
(2) Date: Jun. 1, 2018

(87) PCT Pub. No.: WO2017/093494
PCT Pub. Date: Jun. 8, 2017

(65) Prior Publication Data
US 2018/0271101 A1 Sep. 27, 2018

(30) Foreign Application Priority Data
Dec. 4, 2015 (EP) ..................................... 15306929

(51) Int. Cl.
*A01N 25/28* (2006.01)
*A01N 37/18* (2006.01)
*A01N 37/20* (2006.01)
*A01N 37/44* (2006.01)
*A01N 37/46* (2006.01)
*A01N 51/00* (2006.01)

(52) U.S. Cl.
CPC .............. *A01N 51/00* (2013.01); *A01N 25/28* (2013.01); *A01N 37/18* (2013.01); *A01N 37/44* (2013.01)

(58) Field of Classification Search
CPC ........ A01N 51/00; A01N 37/18; A01N 37/20; A01N 37/46
See application file for complete search history.

(56) References Cited

U.S. PATENT DOCUMENTS

| 7,745,375 | B2 | 6/2010 | Andersch et al. |
| 2006/0211655 | A1 | 9/2006 | Mencke et al. |
| 2006/0252728 | A1 | 11/2006 | Sirinyan et al. |
| 2007/0122437 | A1 | 5/2007 | Hougard et al. |
| 2009/0036407 | A1* | 2/2009 | Taylor .................... A01N 43/56 514/75 |

FOREIGN PATENT DOCUMENTS

AU 2013 237 746 B2 5/2015

OTHER PUBLICATIONS

Faulde et al. (Parasitology Res. 2012; 111(2); 755-765).*
Frederic Darriet et al: Efficacy of six neonicotinoid insecticides alone and in combination with deltamethrin and piperonyl butoxide against pyrethroid-resistant Aedes aegypti and Anopheles gambiae (Diptera: Culicidae) Pest Management Science, vol. 69, No. 8, Dec. 4, 2012 (Dec. 4, 2012), pp. 905-910.
Commanding et al: 1' Jan. 2004 (Jan. 1, 2004), pp. 27-6, XP055240499, Retrieved from the Internet: URL: http://medind.nic.in/maa/t07/i2/maat07i2p120.pdf [retrieved on Jan. 12, 2016].
European Search Report dated Jan. 13, 2016.
U.S. Office Action dated Jan. 4, 2019.

* cited by examiner

*Primary Examiner* — Shirley V Gembeh
(74) *Attorney, Agent, or Firm* — Ipsilon USA, LLP

(57) ABSTRACT

Insecticide composition wherein the active ingredient comprises the combination of a neonicotinoid insecticide, thiamethoxam as synthetic insecticide molecule, and at least one synergistic agent, which is chosen among the insect repellent agents such as DEET and/or IR3535® and present at a molar ratio of said synergistic agent to thiamethoxam comprised between O.OOI and 0.2 in the composition. Synergistic effect is observed at low doses. Use of the insecticide composition wherein said composition is sprayed or deposited on, or impregnated to a support, such as net, fabrics, cloth or tent, in the fight against insects which are harmful to human, to animals and/or to crops, and in particular against pyrethroid, carbanate and/or organophosphate resistant mosquitoes.

12 Claims, 4 Drawing Sheets

INSECTICIDE COMPOSITION INCLUDING THIAMETHOXAM AND A SYNERGISTIC AGENT

RELATED APPLICATION

This application is a National Phase of PCT/EP2016/079608, filed on Dec. 2, 2016, which claims the benefit of priority from EP 15306929.9, filed on Dec. 4, 2015, the entirety of which are incorporated by reference.

FIELD OF THE INVENTION

The present invention relates to new insecticide compositions, in the vector control and particularly against mosquito-borne diseases.

BACKGROUND OF THE INVENTION

Climatic and social changes influence the distribution and the dynamics of mosquito-borne diseases thus contributing to the risk of emergence and resurgence of epidemics (malaria, dengue, chikungunya). For most mosquito-borne diseases, there is to date no vaccine and no curative treatment. The vector control and the prevention of mosquito bites are particularly based on the safe and efficacious use of chemicals. Because mosquitoes become resistant, it is essential to develop new strategies against insects to increase treatment efficacy and to circumvent resistance mechanisms.

Chemicals which have been classically used, up to now, are classified into two main categories, according to their mode of action. In the first category are insect repellent molecules which prevent mosquitoes of approaching their target and in the second category are insecticide molecules which "kill" the mosquitoes.

In the repellent molecule category, the broadly used insect repellent in the world is DEET (N,N-diethyl-3-methylbenzamide, previously named N,N-diethyl-m-toluamide). Other known insect repellents are Icaridin (KBR) and IR3535® (3-[N-Butyl-N-acetyl]-aminopropionic acid, ethyl ester). To be effective against most mosquitoes implies that they have to be usually employed at relatively high concentrations in the compositions to be applied for instance on clothes or nets. However a compromise should be found between efficacy and adverse effects.

As insecticide synthetic molecules, which are widespread used against mosquitoes, molecules are chosen in the pyrethroid, carbamate or organophosphate families. However mosquitoes have become more and more resistant to these chemicals, in particular to the pyrethroid insecticides which have been widely used for house spraying and impregnation of mosquito nets for instance for malaria control. New insecticide candidates are thus searched for.

Recent studies (Bonnet J. et al. (2009) *Multi-function oxidases are responsible for the synergistic interactions occurring between repellents and insecticides in mosquitoes*. Parasites & Vectors 2:17) have described the efficiency of the combination of a non-pyrethroid insecticide (propoxur from the carbamate family) with a repellent (DEET) against the main dengue vector mosquito *Aedes aegypti*.

A first aim of the invention is to provide a new composition which can be used in the control of pyrethroid carbamate, and/or organophosphate resistant mosquitoes.

Another aim of the invention is to provide a composition which can help controlling the mosquito-borne diseases such as malaria, dengue and chikungunya.

Another aim of the invention is to provide an insecticide composition having an optimized insecticide treatment efficacy while reducing doses.

SUMMARY OF THE INVENTION

Within the inventors' search works to understand the mechanism of action of these molecules against mosquitoes, in particular against dengue, malaria and chikungunya mosquito vectors, it has now been found, surprisingly, that a combination of a specific molecule from the neonicotinoïd family (usually used for pests control in crops and inefficient alone against mosquitoes) and an insect repellent at very low concentration may be active as insecticide composition against mosquitoes.

Consequently, the present invention relates to an insecticide composition wherein the active ingredient comprises the combination of:
  thiamethoxam as synthetic insecticide molecule from the neonicotinoïd family, and
  at least one synergistic agent, which is chosen among N,N-diethyl-3-methylbenzamide (DEET), 3-[N-Butyl-N-acetyl]-aminopropionic acid, ethyl ester (IR3535®), and a mixture thereof and present in said composition at a molar ratio of said synergist agent to thiamethoxam comprised between 0.001 and 0.2.

DETAILED DESCRIPTION OF THE INVENTION

More particularly, in the composition of the invention, the molar ratio of said synergist agent to the thiamethoxam molecule is preferably comprised between 0.005 and 0.1, more preferably between 0.01 and 0.1.

For instance, said thiamethoxam is present at a very low concentration, between 10 M and $10^{-5}$ M, and preferably comprised between $10^{-7}$ M and $3.10^{-6}$ M in the composition. Consequently, such a concentration will lessen toxicity for humans or non-target animals.

The synthetic insecticide molecule thiamethoxam from the neonicotinoïd family has never been used alone against mosquitoes and consequently never used for controlling the mosquito-borne diseases such as malaria, dengue and chikungunya.

Advantageously, DEET can be present at a concentration comprised between $3.10^{-8}$ M and $3.10^{-7}$ M in the composition. IR3535® may be present at still lower concentrations, comprised between $3.10^{-9}$ M and $3.10^{-8}$ M in the composition. At these concentrations, both DEET and IR3535® are at a sub-repellent concentrations against insects, i.e. they have no repellent efficacy and no insecticide efficacy alone against insects and particularly against mosquitoes.

The insecticide composition of the present invention may be in a liquid form, the active ingredient being solubilized in an organic phase and/or encapsulated in nano- or microcapsules. It may be configured to be sprayed on, deposited on, or impregnated into a support such as net, fabrics, cloth, tent, or any other material to prevent insects to reach their targets.

The present invention also relates to uses of the above insecticide composition, wherein said composition is sprayed on, deposited on, or impregnated into a support such as net (for instance mosquito net), fabrics, clothes or tent.

The insecticide composition of the invention can therefore be used against insects which are harmful to human, to animals and/or to crops, in particular against insects from the group: diptera, dictyoptera, lepidoptera, orthoptera and hemiptera, thus providing ways of controlling insect vector-borne diseases.

More particularly, the composition of the invention can be used against pyrethroïd resistant mosquitoes, preferably against *Anopheles gambiae* (main vector of malaria) and *Aedes aegypti* (main vector of dengue fever, chikungunya and yellow fever viruses), as well as against mosquitos which are resistant to carbamate and/or organophosphate insecticide.

The resulting main advantage is a better protection with low dose, and therefore an expected reduction of side-effects for humans and non-target animals. Moreover, the composition of the invention being efficient against mosquitoes which are resistant to pyrethroid insecticides, this composition could also be used in a crop protection context.

FIGURES

The invention will be further described in the below embodiments given with reference to the accompanying drawings, in which.

EXAMPLES

Materials and Methods
Insect Neuronal Model

Experiments were carried out on cockroach Dorsal Unpaired Median (DUM) neurons. Cockroach neuronal preparations are commonly used as biomedical models for vertebrates and invertebrates and DUM neurons are, furthermore, electrophysiologically and pharmacologically well characterized since most of the biophysical and pharmacological properties of ionic currents and receptors underlying and modulating their spontaneous action potentials have been established by using the well-known patch-clamp technique.

Figure 1:
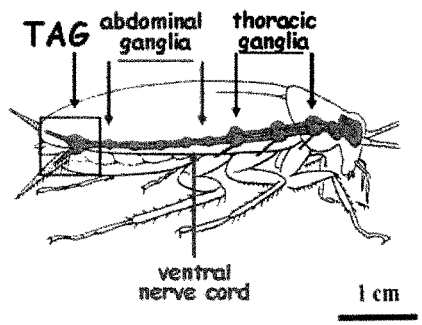
FIG. 1 illustrates the cockroach *Periplaneta americana* central nervous system used in the experiments.

Adult male cockroaches, *Periplaneta americana* (see FIG. 1), are taken from our laboratory colonies, which are maintained under standard conditions (29° C., photoperiod of 12 h light/12 h dark). Animals are immobilized dorsal-side up on a dissection dish. The dorsal cuticle, gut and some dorso-longitudinal muscles are removed to allow access to the ventral nerve cord. The abdominal nerve cord and its terminal abdominal ganglion (TAG), carefully dissected under a binocular microscope, are placed in normal saline. Animal care and handling procedures are in accordance with French institutional and national health guidelines.

The ventral nerve cord and its terminal abdominal ganglion (TAG) are carefully dissected under a binocular microscope and placed in normal cockroach saline containing (in mM) 200 NaCl, 3.1 KCl, 5 CaCl2, 4 MgCl2, 50 sucrose, and 10 N-2-hydroxymethylpiperazine-N9-2-ethanesulfonic acid (HEPES); pH was adjusted to 7.4 with NaOH. Isolation of adult DUM neuron cell bodies are performed under sterile conditions using enzymatic digestion and mechanical dissociation of the median parts of the TAG as previously described in Lapied et al. (*Ionic species involved in the electrical activity of single adult aminergic neurones isolated from sixth abdominal ganglion of cockroach Periplaneta americana* J Exp Biol 144:535-49, 1989). The isolated neuron cell bodies are used for recordings 24 h after dissociation.

Calcium Imaging

Falcon 1006 Petri dishes with glass coverslips are coated with poly-D-lysine hydrobromide (mol. wt. 70,000-150, 000), and isolated DUM neuron cell bodies are plated. External recording solution contains (in mM): 200 NaCl; 3.1 KCl; 5 CaCl2; 4 MgCl2, and 10 HEPES buffer; pH is adjusted to 7.4 with NaOH. The cells are incubated in the dark with 10 µM Fura-2 pentakis (acetoxy-methyl) ester for 60 min at 37° C. After loading, cells are washed three times in saline. The glass coverslips are then mounted in a recording chamber (Warner Instruments, Hamden, Conn.) connected to a gravity perfusion system allowing drug application. Imaging experiments are performed with an inverted microscope (Nikon) equipped with epifluorescence. Excitation light is provided by a 75-W integral xenon lamp. Excitation wavelengths (340 nm and 380 nm) are applied using a computer driven a monochromator (Sutter Instruments Company, Lambda DG4) with a digital charge-coupled device (CCD) camera (Hamamatsu Orca $R^2$) and they are recorded in the computer with calcium imaging software (Imaging Workbench 6, Indec BioSystem). Exposure times at 340 nm and 380 nm are usually 150 ms, and images are collected at various frequencies. Data are expressed as the ratio of emitted fluorescence (340 nm/380 nm). Different concentrations of the insect repellent IR3535® ranging from $10^{-9}$ M to $10^{-5}$ M have been tested.

Electrophysiology and Whole-Cell Patch-Clamp Recordings

Electrical activity and neonicotinoïd-induced inward currents are recorded using the patch clamp technique in the whole-cell recording configuration under current-clamp and voltage-clamp mode, respectively. Patch-clamp electrodes are pulled from borosilicate glass capillary tubes (GC150T-10) using a P-97 model puller. Patch pipettes have resistances ranging from 1 to 1.2 MΩ when filled with internal pipette solution. The liquid junction potential between extracellular and intracellular solutions is always corrected before the formation of a giga Ohm seal (>3GΩ). Signals are recorded with an Axopatch 200A amplifier. Ionic currents induced by thiamethoxam are displayed on a computer with software control pClamp connected to a digidata acquisition system (digidata 1320A). Under voltage-clamp conditions, DUM neuron somata are voltage-clamped at a steady state holding potential of −50 mV to measure the effects of thiamethoxam applied alone and after pretreatment with IR3535® ($10^{-8}$ M). Experiments are carried out at room temperature.

Example 1

1.1—Dose-Dependent Effect of the Insect Repellent IR3535® on Insect Neurons

Using calcium imaging, it has been possible to study the effect of the insect repellent IR3535®, on the intracellular calcium concentration in DUM neurons. Bath application of IR3535® induces a complex multiphasic dose-dependent effect on the intracellular calcium concentration (see FIG. 2).

Figure 2:
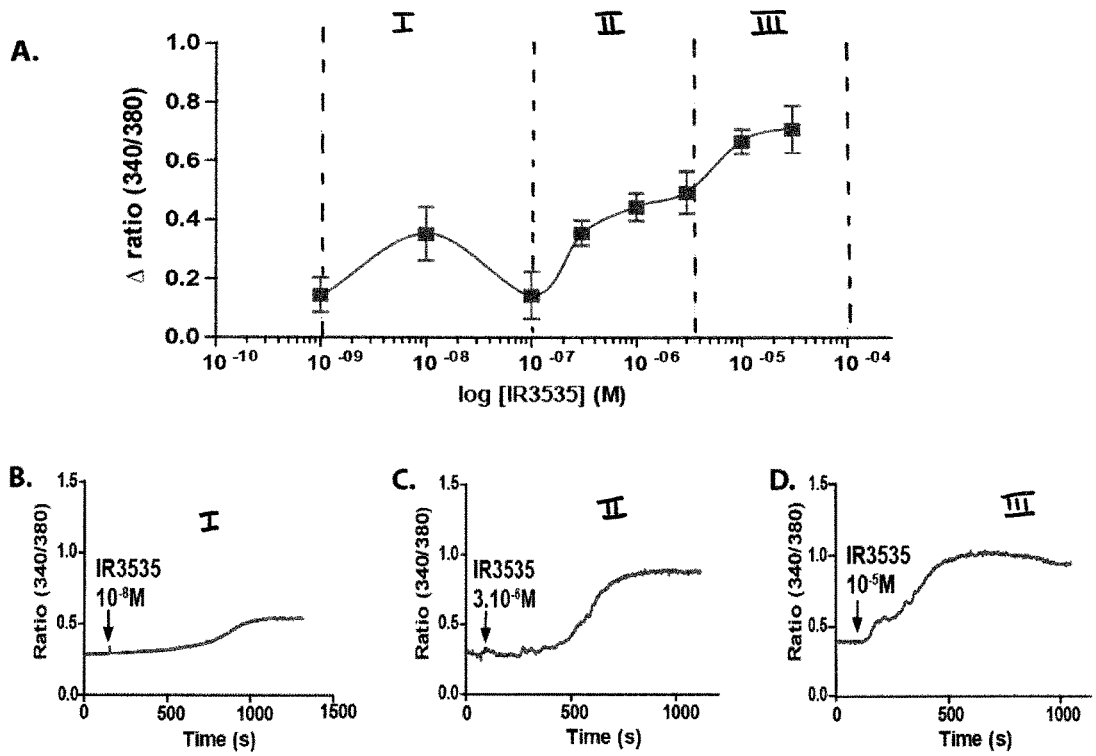
FIG. 2 (A to D) are curves showing the complex dose-dependent effects of IR3535® on DUM neuron intracellular calcium concentration.

FIG. 2 A shows the dose-response curve illustrating changes in intracellular calcium concentration depending on the different concentrations of IR3535® tested. Intracellular calcium concentration variations (presented as ratios 340/380) have been calculated from mean values obtained for each IR3535® concentration tested (n=5). FIG. 2B to D represent spectrum of the intracellular calcium concentration rises induced by IR3535® tested at $10^{-8}$ M, $3.10^{-6}$ M and $10^{-5}$ M, respectively.

In the zone I (FIGS. 2A and 2B), it is possible to observe a transient increase of intracellular calcium concentration between $3.10^{-9}$ M and $3.10^{-8}$ M, reaching a maximum for IR3535® used at $10^{-8}$ M, i.e. at a very low concentration.

Zone II corresponds to an additional elevation of intracellular calcium concentration obtained for IR3535® used in the concentration range from $10^{-7}$ M to $3.10^{-6}$ M (FIGS. 2A and 2C). Finally, zone III corresponds to the maximum effect produced by IR3535® used at very high concentration ($3.10^{-5}$ M) (FIGS. 2A and 2D). These results demonstrate that the insect repellent IR3535® exerts its effect through an elevation of intracellular calcium concentration in insect neurons.

1.2—Origin of the Intracellular Calcium Rise

Figure 3:
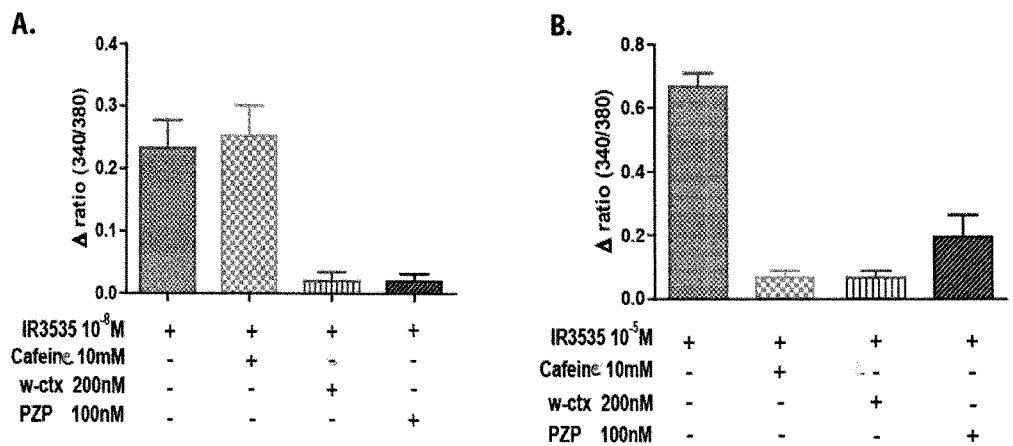
FIG. 3A and FIG. 3B are comparative histograms illustrating the effects of IR3535® used at $10^{-8}$ M (A) and $10^{-5}$ M (B) on the intracellular calcium concentration in the presence of different pharmacological agents.

To determine the origin of the intracellular calcium concentration rise (i.e., intracellular and/or extracellular origin), different specific blockers and/or antagonists of calcium channels and membrane receptors have been tested. Histograms of FIG. 3 show the comparative effects of IR3535® used at $10^{-8}$ M (FIG. 3A) and $10^{-5}$ M (FIG. 3B) on the intracellular calcium concentration in the presence of different pharmacological agents such as caffeine, omegaconotoxin (ω-ctx) and pirenzepine (PZP).

From these results inventors have determined that the effect of IR3535® used at $10^{-8}$ M results from extracellular calcium through plasma membrane voltage-dependent calcium channels via M1/M3 mAChR sub-type modulation. For higher concentrations of IR3535®, both extracellular calcium and calcium released from internal stores are involved in the effects of the repellent in insect neurons.

Figure 4:
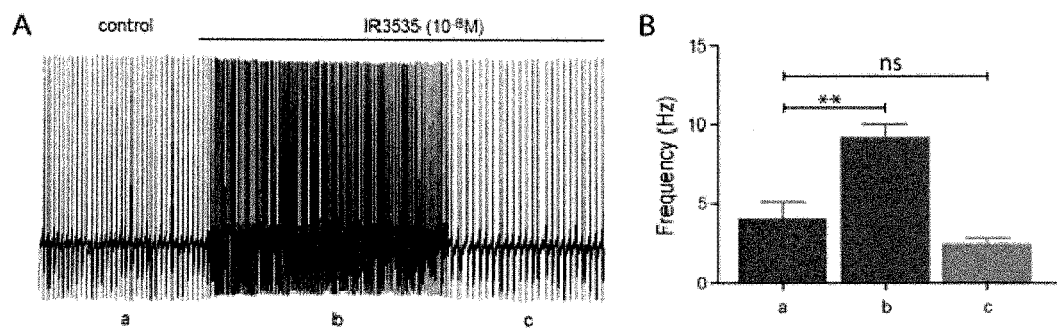
FIG. 4A illustrates the effect of IR3535® used at $10^{-8}$ M on the DUM neuron spontaneous electrical activity and FIG. 4B shows comparative histogram of the effects of IR3535® used at $10^{-8}$ M on action potential discharge frequency.

1.3—Effect of the Insect Repellent IR3535® on DUM Neuron Spontaneous Action Potentials From the data presented just above, it appears that $10^{-8}$ M is the lower concentration of IR3535®, which produces a significant elevation of intracellular calcium concentration in DUM neurons. Consequently, the following experiments have been performed using $10^{-8}$ M IR3535®. Using the patch clamp technique in the whole-cell recording configuration, it has been possible to show that IR3535® ($10^{-8}$ M) induces a significant membrane depolarization associated with an increase of the spontaneous action potential discharge frequency (FIG. 4A). The corresponding FIG. 4B illustrates comparative histogram of the effect of IR3535® ($10^{-8}$ M) on the spontaneous action potential discharge frequency.

According to the results presented above, using different pharmacological agents, calcium imaging and electrophysiological technique, and based on previous results obtained on the same neuronal preparation, it is possible to summarize the effect of IR3535® used at very low concentration on the intracellular calcium concentration in DUM neurons. IR3535®, by acting on M1/M3 mAChR sub-types, inhibits background calcium-activated potassium channels resulting in the small depolarization observed. This membrane depolarization is sufficient to stimulate N-type high-voltage activated calcium channels involved in the calcium influx through the membrane.

Example 2—Dose-Dependent Effect of the Insect Repellent DEET on Insect Neurons Similar experiments as example 1 have been made with DEET at different concentrations.

Application of the insect repellent DEET onto insect neurons produces a biphasic effect on the intracellular calcium concentration changes. In the low concentration range (from $10^{-9}$ M to $10^{-7}$ M), DEET induces an elevation of the intracellular calcium concentration reaching a maximum at $10^{-7}$ M DEET (ratio of emitted fluorescence (340 nm/380 nm) ranging from 0.4 to 0.6 with a maximum value of 0.7).

For higher concentrations than $10^{-7}$ M, DEET produces an opposite effect (i.e., an important decrease of the intracellular calcium concentration).

Therefore, preferred concentrations of DEET as synergist agent should be chosen between 3. 10-8 M and 3. 10-7 M where the ratio of emitted fluorescence (340 nm/380 nm) is above 0.6.

Example 3—Synergistic Effect Occurring Between IR3535®/Thiamethoxam

Figure 5:
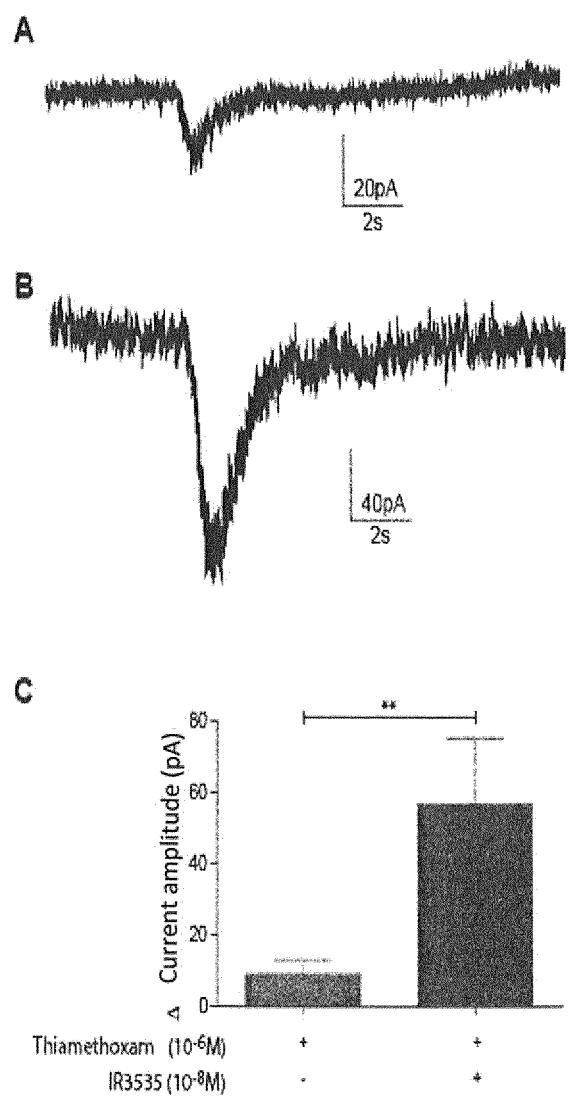
FIG. 5 illustrates the effect of thiamethoxam-induced inward currents ($10^{-6}$ M), recorded under voltage-clamp condition, before (A) and after pretreatment with IR3535® used at $10^{-8}$ M (B), (C) illustrates comparative histogram of the effect of IR3535® ($10^{-8}$ M) on the thiamethoxam-induced inward current amplitude.

The neonicotinoïd insecticide thiamethoxam has been tested alone and after pretreatment with IR3535® ($10^{-8}$ M) on DUM neurons using the patch-clamp technique, under voltage clamp condition (FIG. 5).

Application of thiamethoxam ($10^{-6}$ M) alone induces an inward current with small amplitudes (see FIGS. 5A and 5C: recorded under voltage-clamp condition, at a holding potential of −50 mV, means+S.E.M., **, $p<0.01$; n=3-4).

By contrast, after pretreatment of DUM neuron with the repellent IR3535® used at $10^{-8}$ M, an important increase of the thiamethoxam-induced inward current amplitude is observed. In this case, the mean current amplitude is about 6-fold more important than the current amplitude obtained with thiamethoxam applied alone (FIGS. 5B and 5C).

In conclusion, the complementary approaches such as calcium imaging and electrophysiology reveal that the neonicotinoïd insecticide thiamethoxam acts like an agonist able to induce an inward current with a small amplitude. When DUM neurons are pretreated with low concentration of IR3535®, the inward current amplitude produces by thiamethoxam is more important. This confirms the role of IR3535® as synergistic agent, which can increase the effect of thiamethoxam via an increase of intracellular calcium concentration. These results confirm that combining the repellent IR3535® with the molecule thiamethoxam could be an interesting alternative to 1) circumvent resistance mechanisms developed by mosquitoes-borne diseases and 2) increase insecticide efficacy while reducing doses.

Example 4—Pretreatment with Acetylcholine

Acetylcholine at a concentration of $10^{-3}$ M has been applied to DUM neurons during one second, three minutes before testing thiamethoxam at $10^{-7}$M, $10^{-6}$M and $10^{-5}$M on DUM neurons under the same protocol as example 3.

Figure 6:
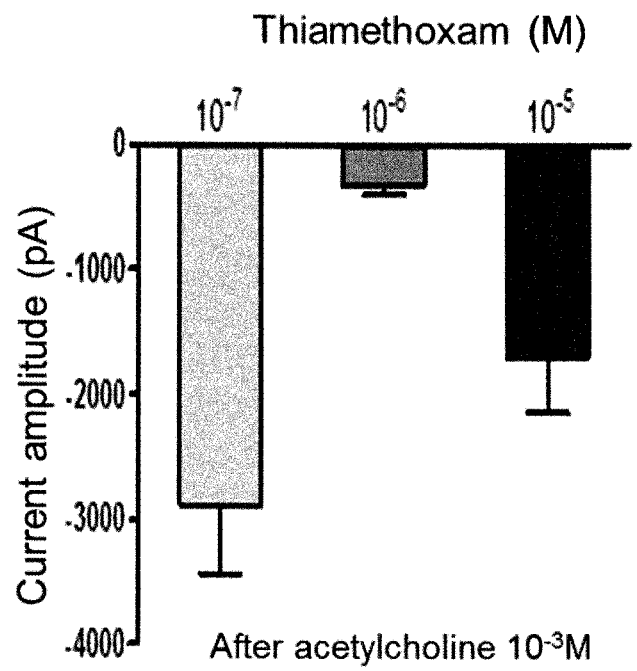
FIG. 6 is a comparative histogram of the effect of thiamethoxam at different concentrations on insect neuron after pretreatment with acetylcholine $10^{-3}$M.

Although no current has been recorded with thiamethoxam alone, thiamethoxam after pretreatment with acetylcholine induces a current the amplitude of which amplitude is reported in histogram of FIG. 6. This suggests that acetylcholine, acting on the cholinergic receptors of the neurons, leads to an increase of the intercellular calcium that induces the effect of thiamethoxam shown by the observed current.

FIG. 6 shows that the current amplitude is at the highest value for thiamethoxam $10^{-7}$M and the lowest value for thiamethoxam $10^{-6}$M.

Figure 7:
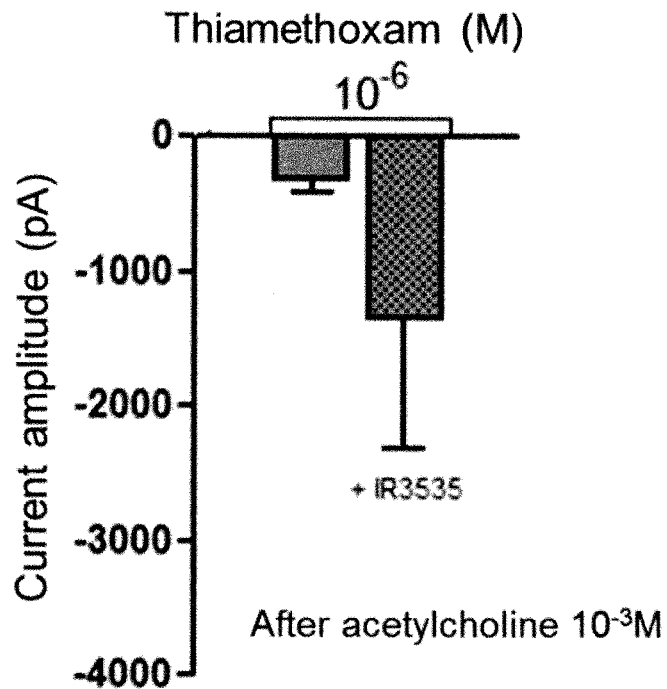
FIG. 7 is an histogram illustrating the effects of IR3535®/thiamethoxam mixture on insect neuron after pretreatment with acetylcholine $10^{-3}$M.

However, at this concentration of thiamethoxam $10^{-6}$M, when combined with IR3535® at $10^{-8}$M, (after a pretreatment with acetylcholine $10^{-3}$M), a synergist effect is observed (see histogram of FIG. 7).

From the above results, it can be concluded that the well know insect repellent IR3535® is able to potentiate the neurotoxic effect of the neonicotinoid thiamethoxam. Example 4 clearly indicates that the potentiation is more effective when the neurons are pretreated with the endogenous neurotransmitter acetylcholine. In fact, acetylcholine is known to increase the intracellular calcium concentration. Pre-treatments with both acetylcholine and IR3535® reinforce the synergistic effect, via the intracellular calcium rise. These results are very interesting since the endogenous acetylcholine level and/or the density of targets affected by thiamethoxam seem to be different between the wild population of mosquito *A. gambiae* (named Kis) and mosquitoes resistant to insecticides such as organophosphates and/or carbamates (named AcerKis). In this case, application of such IR3535/thiamethoxam mixture on resistant mosquitoes AcerKis will be very efficient to increase the mortality rate of these mosquitoes and to overcome the resistance mechanism.

In other words, the above results may indicate that the repellent/insecticide composition of the present invention would be more efficient against resistant mosquitoes than "wild" mosquitoes.

The invention claimed is:

1. Insecticide composition comprising:
    an active ingredient that includes the combination of thiamethoxam as synthetic insecticidal molecule, and
    at least one synergistic agent selected from the group consisting of N,N-diethyl-3-methylbenzamide (DEET) at a concentration comprised between $3.10^{-8}$ M and $3.10^{-7}$ M in the composition, 3-[N-Butyl-N-acetyl]-aminopropionic acid ethyl ester (IR3535®) at a concentration comprised between $3.10^{-9}$ M and $3.10^{-8}$ M in the composition, and a mixture thereof and present in the composition at a ratio of 0.001 and 0.2 between a molar amount of said synergistic agent to a molar amount of thiamethoxam.

2. Insecticide composition according to claim 1, wherein, in the present composition, the ratio between the molar amount of said synergist agent to the molar amount of thiamethoxam in the composition is 0.005 and 0.1.

3. Insecticide composition according to claim 1, wherein thiamethoxam is present at a concentration comprised between $10^{-7}$ M and $3.10^{-6}$ M in the composition.

4. Insecticide composition according to claim 2, wherein the molar ratio of said synergist agent to thiamethoxam in the composition is comprised between 0.01 and 0.1.

5. Insecticide composition according to claim 2, wherein the molar ratio of said synergist agent to thiamethoxam in the composition is comprised between 0.01 and 0.05.

6. Insecticide composition according to claim 1, wherein said composition is in a liquid form, the active ingredient being solubilized in an organic phase and/or encapsulated in nano- or micro-capsules.

7. Insecticide composition according to claim 1, wherein said composition is configured to be sprayed or deposited on, or impregnate a support, such as net, fabrics, cloth or tent.

8. Insecticide composition according to claim 1, wherein said composition is configured to be applied against insects which are harmful to human, to animals and/or to crops, including insects chosen from the group consisting of: diptera, dictyoptera, lepidoptera, orthoptera and hemiptera.

9. The insecticide composition as claimed in claim 8 wherein said insecticide composition is configured to be applied against pyrethroid resistant mosquitoes.

10. The insecticide composition as claimed in claim 8 wherein said insecticide composition is configured to be applied against mosquitos which are resistant to carbamate and/or organophosphate insecticide.

11. The insecticide composition as claimed in claim 8 wherein said insecticide composition is configured to be applied against *Aedes aegypti* or *Anopheles gambiae*.

12. The insecticide composition as claimed in claim 8 wherein said insecticide composition is configured to be applied for controlling mosquito-borne diseases.

* * * * *